US00PP20525P3

(12) United States Plant Patent
Blom

(10) Patent No.: US PP20,525 P3
(45) Date of Patent: Dec. 8, 2009

(54) ***CHRYSANTHEMUM* PLANT NAMED 'ZANMUSPAR'**

(50) Latin Name: *Chrysanthemum×Morifolium*
Varietal Denomination: Zanmuspar

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/003,595

(22) Filed: Dec. 28, 2007

(65) Prior Publication Data

US 2009/0172850 P1 Jul. 2, 2009

(51) Int. Cl.
*A01H 5/00* (2006.01)

(52) U.S. Cl. ..... Plt./294

(58) Field of Classification Search ..... Plt./294

See application file for complete search history.

*Primary Examiner*—David H Kruse
*Assistant Examiner*—June Hwu
(74) *Attorney, Agent, or Firm*—Steptoe & Johnson LLP

(57) ABSTRACT

A *chrysanthemum* plant named 'Zanmuspar' characterized by its medium sized blooms with white ray florets and a yellow center, and prolific branching; natural season flower date September 24; blooming for a period of 5 weeks.

3 Drawing Sheets

Botanical designation: *Chrysanthemum×morifolium* Ramat.

Cultivar denomination: 'Zanmuspar'.

BACKGROUND OF THE INVENTION

The present invention relates to a new and distinct cultivar of *chrysanthemum* plant, botanically known as *Chrysanthemum×morifolium* Ramat., commercially grown as a garden mum, and herein after referred to by the cultivar denomination 'Zanmuspar'. 'Zanmuspar' is a product of a breeding and selection program for outdoor pot mums (garden mums) which had the objective of creating new *chrysanthemum* cultivars with a semi-double type flower, a natural season flower date around September 24; blooming for a period of 5 weeks. 'Zanmuspar' is a seedling resulting from a crossing of the seed parent id 15.836 and pollen parent id 647. Plants of the new cultivar 'Zanmuspar' differ mainly from the parent plants in natural-season flowering. The plants of 'Zanmuspar' flower in mid-season, while those of the seed parent flower in early-season, and those of the pollen parent in late-season. The new and distinct cultivar was discovered and selected as a flowering plant by Wilhelmus Bernardus Blom on a cultivated field in Rijsenhout, The Netherlands in 2004. The first act of asexual production of 'Zanmuspar' was accomplished when vegetative cuttings from the initial selection in 2004 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
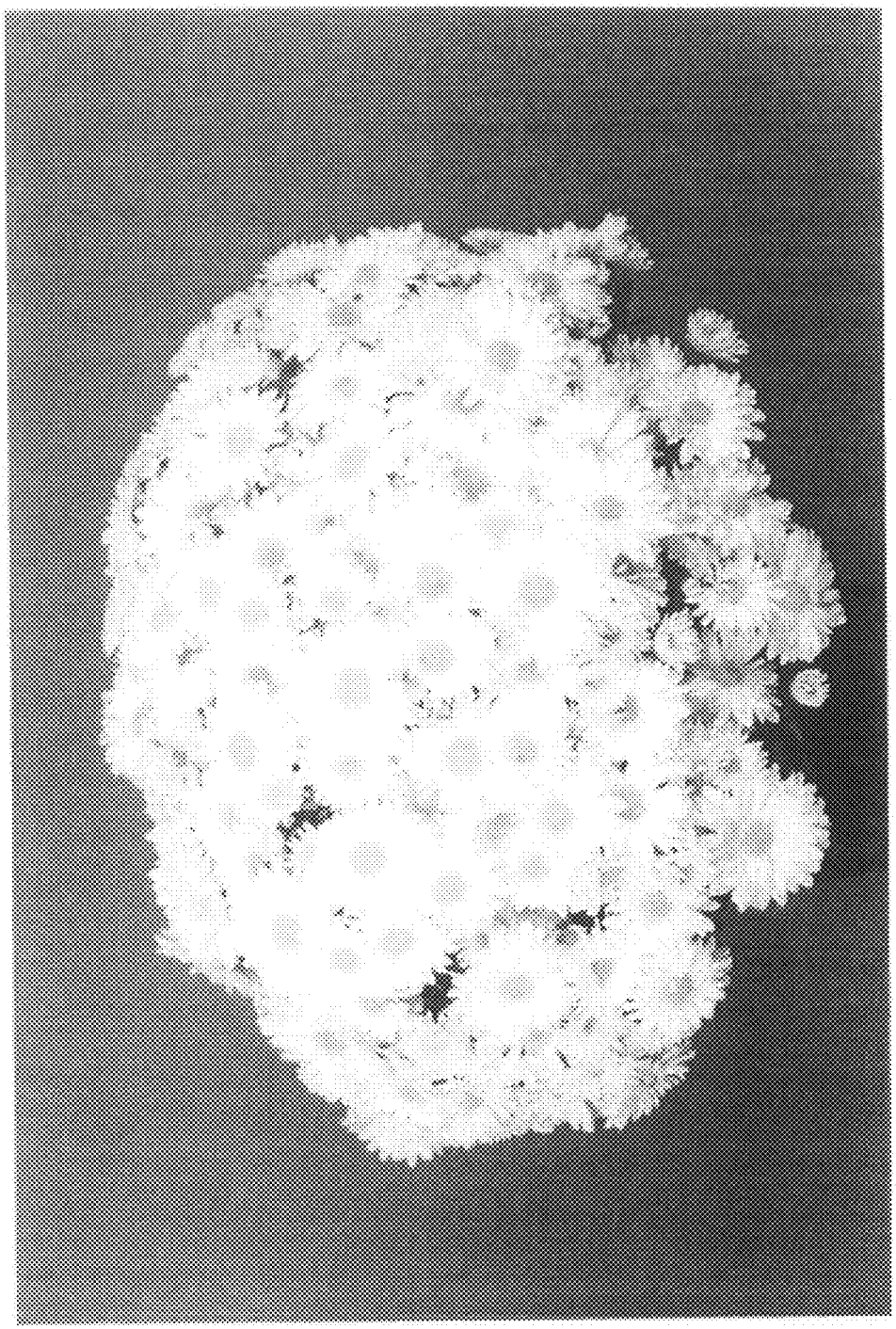
FIG. 1 shows a plant of the cultivar in full bloom.
Figure 2:
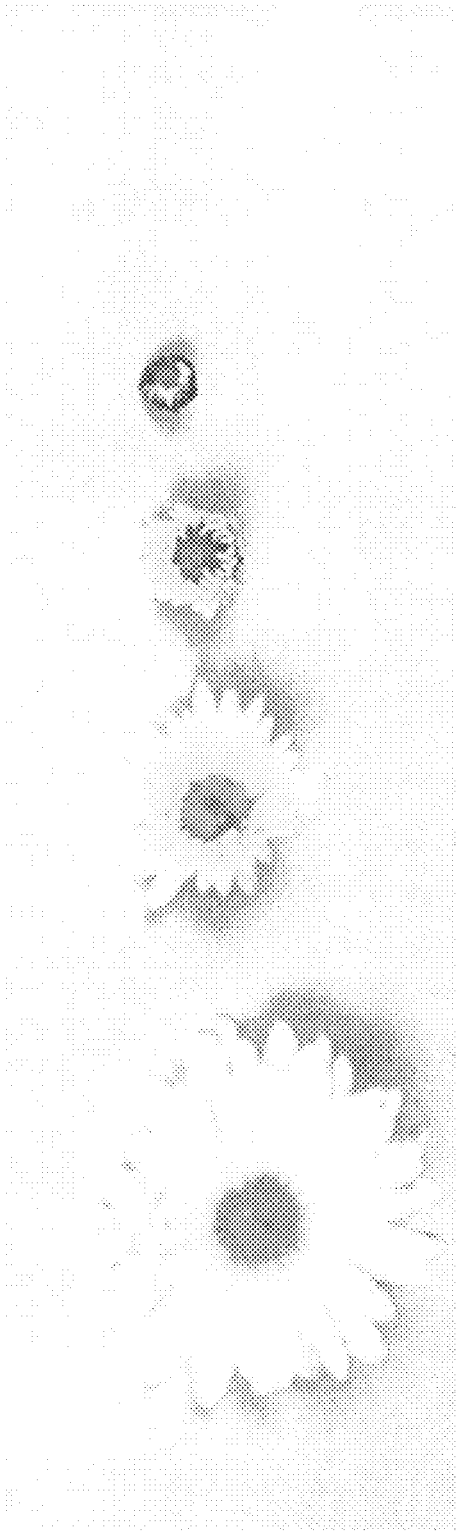
FIG. 2 shows the various stages of bloom of the new cultivar.
Figure 3:
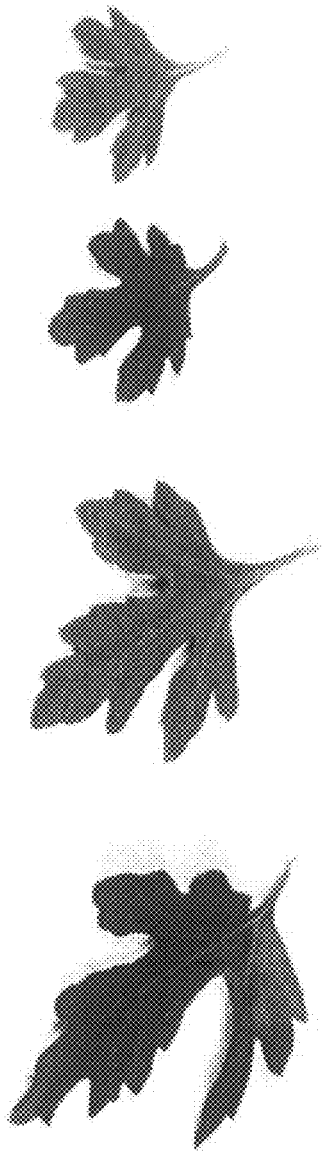
FIG. 3 shows the various stages of foliage of the new cultivar.

The observations and measurements were gathered from plants grown out door in Rijsenhout, The Netherlands under natural day length and temperature and planted in week 25 in 2007. The natural blooming date of this crop was September 24 (week 39). The average height of the plants was 35 cm. No growth retardants were used. No tests were done on disease or insect resistance or susceptibility. No tests were done on cold or drought tolerance. This new variety produces medium sized blooms with white ray florets and a yellow center blooming for a period of 5 weeks.

From the cultivars known to inventor the most similar existing cultivar in comparison to 'Zanmuspar' is 'Starlet White' (U.S. Plant Pat. No. 16,470). When 'Starlet White' and 'Zanmuspar' are being compared the following difference is noticed: The difference of 'Starlet White' and 'Zanmuspar' are (1) Number of blooms And (2) Ray-floret length (1) The number of blooms per branch is higher in 'Starlet White' than in 'Zanmuspar'. (2) The ray-florets of 'Zanmuspar' are longer than those of 'Starlet White'.

The following is a description of the plant and characteristics that distinguish 'Zanmuspar' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Botanical description of *chrysanthemum* plant named 'Zanmuspar' | |
|---|---|
| Bud | |
| Size | Small ;cross-section 0.4 cm, height 0.6 cm |
| Outside Color | Yellow-white 158D |
| Phyllaries | 2 rows |
| Phyllaries among disc-florets | Not present |
| Bloom | |
| Type | Semi-double |
| Height | 1.5 cm |
| Size | 5.5 cm |
| Phyllary number | 10-12 |
| Phyllary color (upper surface) | Green 138A |
| Phyllary length and width | length 7 mm, width 3 mm |
| Peduncle length | 3.5 cm |
| Peduncle color | Greyed-green 189B |
| Number of blooms per branch | Approx. 8-10 blooms per branch |
| Duration of flowering | 5 weeks |
| Seeds | Produced in small quantities, ovate grey-brown 199A, 1½ mm in length. |
| Fragrance | Typical *chrysanthemum*, slightly |
| Color | |
| Center of the flower (disc florets) | Immature stage: Yellow-green 144B<br>Mature stage: Yellow-orange 16A |
| Color of upper surface of the ray-florets | White 155D |
| Color of the lower surface of the ray-florets | White 155D |
| Tonality from Distance | A garden mum with white flowers and yellow center |
| Color of the ray-florets after aging of the plant | White 155D |
| Ray florets | |
| Texture | Upper and under side smooth |
| Number | 68-70 |
| Cross-section | Flat |
| Longitudinal axis of majority | Straight |
| Length of corolla tube | 0.3 cm |
| Ray-floret margin | Entire |
| Ray-floret length | 2-2.2 cm |
| Ray-floret width | 0.3-0.5 cm |
| Ratio length/width | High |
| Shape of tip | Dentate |
| Disc florets | |
| Disc diamter | 1 cm |
| Distribution of disc florets | Many, clearly visible in all stages of flowering |
| Shape | Tabular |
| Color | Yellow-green 144B at upper part;<br>Yellow 11D at base |
| Receptacle shape | Conical raised |
| Reproductive Organs | |
| Stamen | Present in disc florets only |
| Stamen color | Yellow-green 144A |
| Pollen | Present |
| Pollen color | Yellow 7A |
| Number of pistil per ray-florets | One |
| Styles | Present in both ray- and disc florets |

TABLE 1-continued

| Botanical description of *chrysanthemum* plant named 'Zanmuspar' | |
|---|---|
| Style color | Yellow 13A |
| Style Length | 4 mm |
| Stigma color | Yellow-green 144A |
| Stigma Width | 1 mm |
| Ovaries | Enclosed in calyx |
| Plant | |
| Form | Grown as a spray type pot mum, outdoor mounded and round |
| Growth habit | Spherical shape |
| Growth rate | Vigorous |
| Height | 35 cm |
| Width | 50 cm |
| Stem Color | Greyed-brown 199C |
| Stem Strength | Strong |
| Stem Brittleness | Not brittle |
| Stem Anthocyanin Coloration | Absent |
| Internode length | 1-2 cm |
| Length of lateral branch | From top to bottom 16-18 cm |
| Lateral branch color | Yellow-green 138B |
| Lateral branch, attachment | Strong |
| Branching (average number of lateral branches) | Good with 7-8 breaks after pinching |
| Natural season blooming date | September 24 |
| Foliage | |
| Leaf color | Upper side: Green 139A<br>Lower side: Green N138B |
| Color midvein | Upper side: Yellow-green 147D<br>Lower side: Yellow-green 148D |
| Size | Small.; length 4.5-7 cm, width 3-5 cm |
| Quantity (number per lateral branch) | 15-17 |
| Shape | Ovate |
| Texture upper side | Glabrous |
| Texture under size | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronulate |
| Petiole length | 0.5-1 cm |
| Petiole color | Yellow-green 148D |

TABLE 2

| Differences with the comparison variety | | |
|---|---|---|
| | 'Zanmuspar' | 'Starlet White' |
| Number of blooms per branch | 11-20 | 8-10 |
| Length ray-floret | 2-2.5 cm | 1.5-1.8 cm |

The invention claimed is:

1. A new and distinct variety of *chrysanthemum* plant as described and illustrated.

* * * * *